United States Patent
Drewes et al.

[11] Patent Number: 6,100,420
[45] Date of Patent: *Aug. 8, 2000

[54] HETEROCYCLYLBENZONITRILES

[75] Inventors: Mark-Wilhelm Drewes; Roland Andree, both of Langenfeld; Kurt Findeisen, Leverkusen; Wilhelm Haas, Pulheim; Andreas Lender, Wuppertal; Karl-Heinz Linker, Leverkusen; Otto Schallner, Monheim; Markus Dollinger; Hans-Joachim Santel, both of Leverkusen, all of Germany

[73] Assignee: Bayer Aktiengesellschaft, Leverkusen, Germany

[*] Notice: This patent issued on a continued prosecution application filed under 37 CFR 1.53(d), and is subject to the twenty year patent term provisions of 35 U.S.C. 154(a)(2).

[21] Appl. No.: 09/153,715

[22] Filed: Sep. 15, 1998

Related U.S. Application Data

[62] Division of application No. 08/727,501, filed as application No. PCT/EP95/01441, Apr. 18, 1995.

[30] Foreign Application Priority Data

Apr. 27, 1994 [DE] Germany .............................. 44 14 568

[51] Int. Cl.⁷ ................................................. C07C 255/07
[52] U.S. Cl. .......................................................... 558/413
[58] Field of Search ............................................... 558/413

[56] References Cited

U.S. PATENT DOCUMENTS 5,221,318 6/1993 Fischer et al. .
5,681,794 10/1997 Andree et al. ........................... 504/243
5,756,805 5/1998 Schallner et al. ....................... 558/413

FOREIGN PATENT DOCUMENTS 0 364 797   4/1990   European Pat. Off. .
0 370 332   5/1990   European Pat. Off. .
0 558 999   9/1993   European Pat. Off. .
0 648 772   4/1995   European Pat. Off. .

OTHER PUBLICATIONS

Cram & Hammond, "Organic Chemistry", McGraw Hill Book Co., NY (1964) 2nd ed., pp. 565–567.

Primary Examiner—Patricia L. Morris
Attorney, Agent, or Firm—Norris McLaughlin & Marcus

[57] ABSTRACT

The invention relates to new heterocyclylbenzonitriles of the general formula (I)

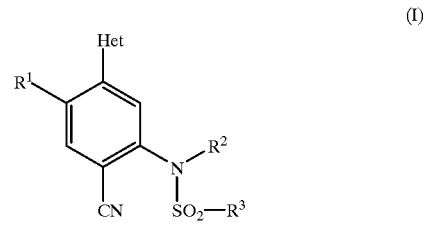

in which $R^1$, $R^2$, $R^3$ and Het have the meanings given in the description, new processes and new intermediate products for their preparation and their use as herbicides.

1 Claim, No Drawings

HETEROCYCLYLBENZONITRILES

This application is a divisional of U.S. application Ser. No. 08/727,501, filed on Oct. 21, 1996 (now allowed), now U.S. Pat. No. 5,858,925, which is a 371 of PCT/EP95/01441 filed on Apr. 18, 1995.

The invention relates to new heterocyclylbenzonitriles, processes and new intermediate products for their preparation and their use as herbicides.

It is already known that certain heterocyclylbenzonitriles, such as, for example, the compounds 2,5-difluoro-4-(4,5,6,7-tetrahydro-3-methyl-2H-indazol-2-yl)-benzonitrile and 4-[5-(t-butyl)-2-oxo-1,3,4-oxadiazol-3(2H)-yl]-2,5-difluorobenzonitrile, have herbicidal properties (cf. EP-A 370332, Examples 2 and 7; cf. also EP-A 364797 and EP-A 558999). However, the activity of these compounds which are already known is not completely satisfactory in all fields of use, especially when low amounts are applied and at low concentrations.

The new heterocyclylbenzonitriles of the general formula (I)

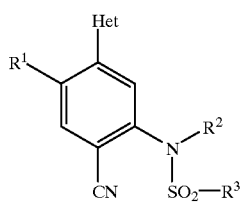

(I)

in which $R^1$ represents hydrogen or halogen, $R^2$ represents hydrogen or represents formyl, or represents in each case optionally substituted alkyl, alkenyl, alkinyl, alkoxy, alklylcarbonyl, alkoxycarbonyl, alkylsulphonyl, cycloalkyl, cycloalkylalkyl, cycloalkylcarbonyl, cycloalkylsulphonyl, arylalkyl, arylcarbonyl, arylalkylcarbonyl, aryloxycarbonyl, arylsulphonyl, arylallylsulphonyl or heteroarylsulphonyl, $R^3$ represents in each case optionally substituted allyl, cycloalkyl, aryl, arylalkyl or heteroaryl and Het represents one of the heterocyclic grouping listed below (bonded via N)

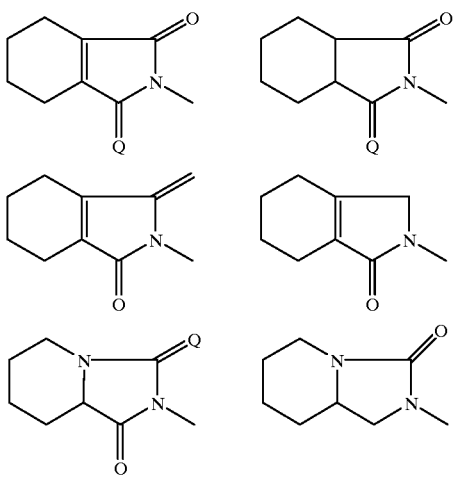

-continued

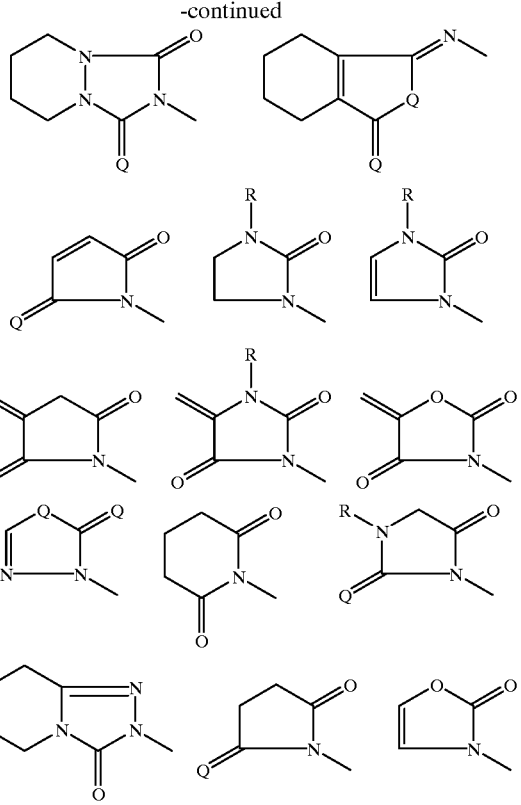

wherein, in each case, where appropriate,

A represents $C_1$–$C_4$-alkanediyl which is optionally interrupted by $SO_2$ and Q represents oxygen or sulphur, and wherein the heterocyclic groupings mentioned in each case are optionally substituted once to four times by identical or different radicals from the series consisting of hydroxyl, halogen, cyano, nitro, $C_1$–$C_4$-alkyl, $C_1$–$C_4$-halogenoalkyl, $C_1$–$C_4$-alkoxy, $C_1$–$C_4$-halogenoalkoxy or phenyl, and R represents a radical from the series consisting of hydrogen, hydroxyl, cyano, nitro, $C_1$–$C_4$-alkl, $C_1$–$C_4$-halogenoalkyl, $C_1$–$C_4$-alkoxy, $C_1$–$C_4$-halogenoalkoxy or phenyl, have now been found.

It has furthermore been found that heterocyclylbenzonitriles of the general formula (I) are obtained by a procedure in which (a) anhydrides of the general formulae (IIa) to (IIg)

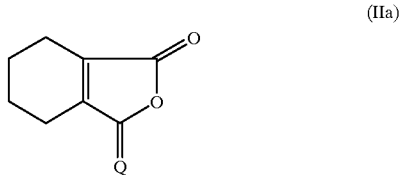

(IIa)

-continued

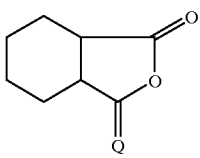
(IIb)

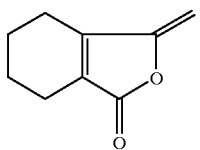
(IIc)

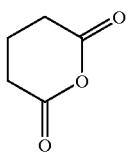
(IId)

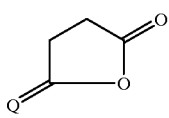
(IIe)

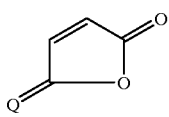
(IIf)

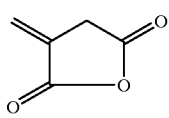

(IIg)

in which

Q has the abovementioned meaning, are reacted with aminobenzonitriles of the general formula (III)

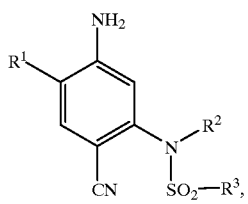
(III)

in which $R^1$, $R^2$ and $R^3$ have the abovementioned meanings, if appropriate in the presence of a diluent and if appropriate in the presence of a reaction auxiliary, or by a procedure in which (b) halogenated heterocyclylbenzonitriles of the general formula (IV)

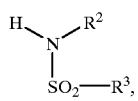
(IV)

in which

Het and $R^1$ have the abovementioned meanings and $X^1$ represents halogen, are reacted with sulphonamides of the general formula (V)

$$\underset{SO_2-R^3,}{H\diagdown N \diagup R^2}$$ (V)

in which $R^2$ and $R^3$ have the abovementioned meanings, if appropriate in the presence of a diluent and if appropriate in the presence of an acid acceptor.

The new heterocyclylbenzonitriles of the general formula (I) are distinguished by a potent herbicidal activity.

Surprisingly, the compounds of the formula (I) according to the invention show a considerably more potent action against weeds, coupled with a good tolerance with respect to crop plants, such as, for example, barley, than the structurally similar compounds 2,5-difluoro-4-(4,5,6,7-tetrahydro-3-methyl-2H-indazol-2-yl)-benzonitrile and 4-[5-(t-butyl)-2-oxo-1,3,4-oxadiazol-3(2H)-yl]-2,5-difluoro-benzonitrile known from the prior art.

In the definitions, the saturated or unsaturated hydrocarbon chains, such as alkyl, alkenyl or alkinyl, are in each case straight-chain or branched.

Halogen in general represents fluorine, chlorine, bromine or iodine, preferably fluorine, chlorine or bromine, in particular fluorine or chlorine.

The invention preferably relates to compounds of the formula (I) in which $R^1$ represents hydrogen or halogen, $R^2$ represents hydrogen, or represents formyl, or represents alkyl, alkenyl, alkinyl, alkoxy, alkylcarbonyl, alkoxycarbonyl or alkylsulphonyl having in each case up to 6 carbon atoms and in each case optionally substituted by halogen, cyano, $C_1$–$C_4$-alkoxy or $C_1$–$C_4$-alkoxy-carbonyl, or represents cycloalkyl, cycloalkylalkyl, cycloalkylcarbonyl or cycloalkylsulphonyl having 3 to 6 carbon atoms in the cycloalkyl part and, where appropriate, 1 to 4 carbon atoms in the alkyl part and in each case optionally substituted by halogen, cyano or $C_1$–$C_4$-alkyl, or represents phenylmethyl, phenylcarbonyl, naphthylcarbonyl, phenylmethylcarbonyl, phenoxycarbonyl, phenylsulphonyl, naphthylsulfonyl, phenylmethylsulphonyl, thienylsulphonyl, pyrazolylsulphonyl, pyridinylsulphonyl or pyridinylmethylsulphonyl (which are in each case optionally substituted by halogen, cyano, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxycarbonyl), $R^3$ represents alkyl, alkenyl or alkinyl having in each case up to 10 carbon atoms and in each case optionally substituted by halogen, cyano or $C_1$–$C_4$-alkoxy, or represents cycloalkyl or cycloalkylalkyl having 3 to 8 carbon atoms in the cycloalkyl part and, where appropriate, 1 to 4 carbon atoms in the alkyl part and in each case optionally substituted by halogen, cyano or $C_1$–$C_4$-alkyl, or represents aryl or arylalkyl having 6 or 10 carbon atoms in the aryl part and 1 to 4 carbon atoms in the alkyl part and in each case optionally substituted by halogen, cyano, nitro, carboxyl or carbamoyl, by $C_1$–$C_4$-alkyl, $C_1$–$C_4$-alkoxy, $C_1$–$C_4$-alkylthio, $C_1$–$C_4$-alkylsulphinyl or $C_1$–$C_4$-alkylsulphonyl (which are in each case optionally substituted by fluorine and/or chlorine), or by dimethylaminosulphonyl, diethylaminosulphonyl, dimethylaminocarbonyl or diethylaminocarbonyl, or by $C_1$–$C_4$-alkoxy carbonyl (which is optionally substituted by halogen, methoxy or ethoxy), or by phenyl, phenyloxy or phenylthio (which are in each case optionally substituted by halogen, cyano, methyl, methoxy, trifluoromethyl and/or trifluoromethoxy), or represents heterocyclyl or heterocyclylalkyl having 2 to 6 carbon atoms and 1 to 4 nitrogen atoms and/or 1 to 2 oxygen or sulphur atoms in the sated or unsaturated heterocyclyl part and, where appropriate, 1 to 4 carbon atoms in the alkyl part and in each case optionally substituted by halogen, cyano, nitro, carboxyl or carbamoyl, or by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl or $C_1$–$C_4$-alkoxycarbonyl (which are in each case optionally substituted by halogen) or by phenyl, phenoxy or phenylthio (which are in each case optionally substituted by halogen, cyano, $C_1$–$C_4$-allyl, $C_1$–$C_4$-halogenoalkyl, $C_1$–$C_4$-alkoxy and/or $C_1$–$C_4$-halogenoalkoxy), and Het represents one of the heterocyclic groupings listed below (bonded via N)

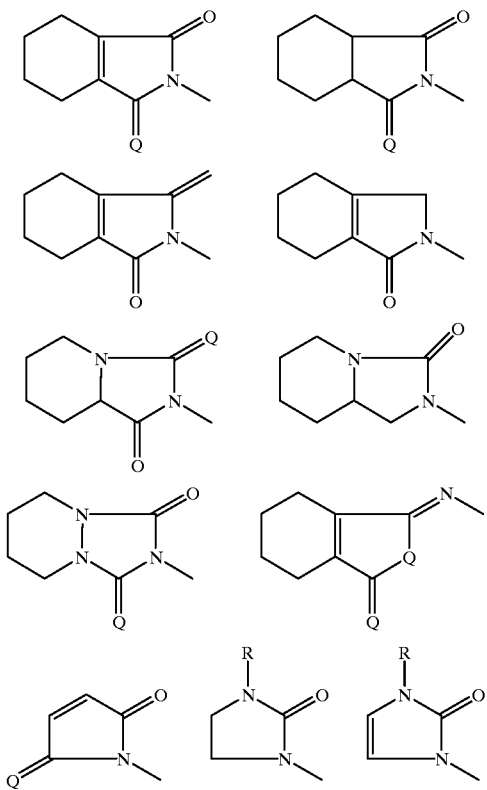

-continued

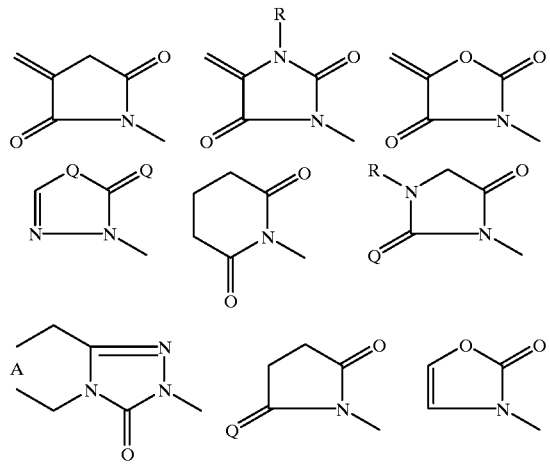

wherein, in each case, where appropriate,

A represents $C_1$–$C_3$-alkanediyl which is optionally interrupted by $SO_2$ and Q represents oxygen or sulphur, and wherein the heterocyclic groupings mentioned are in each case optionally substituted once to three times by identical or different radicals from the series consisting of hydroxyl, halogen, cyano, nitro, $C_1$–$C_4$-alkyl, $C_1$–$C_4$-halogenoalkyl, $C_1$–$C_4$-alkoxy, $C_1$–$C_4$-halogenoalkoxy or phenyl and R represents a radical from the series consisting of hydrogen, hydroxyl, cyano, nitro, $C_1$–$C_4$-alkyl, $C_1$–$C_4$-halogenoalkyl, $C_1$–$C_4$-alkoxy, $C_1$–$C_4$-halogenoalkoxy or phenyl.

The invention particularly relates to compounds of the formula (I) in which $R^1$ represents hydrogen, fluorine or chlorine, $R^2$ represents hydrogen, or represents formyl, or represents methyl, ethyl, n- or i-propyl n-, i-, s- or t-butyl, propenyl, butenyl, propinyl, butinyl, methoxy, ethoxy, n- or i-propoxy, n-, i- or s-butoxy, acetyl, propionyl, butyroyl, methoxycarbonyl, ethoxycarbonyl, n- or i-propoxycarbonyl, methylsulphonyl, ethylsulphonyl, n- or i-propylsulphonyl or n-, i-, s- or t-butylsulphonyl, in each case optionally substituted by fluorine, chlorine, cyano, methoxy, ethoxy, methoxycarbonyl or ethoxycarbonyl, or represents cyclopropyl, cyclobutyl, cyclopentyl, cyclohexyl, cyclopropylmethyl, cyclobutylmethyl, cyclopentylmethyl, cyclohexylmethyl, cyclopropylcarbonyl, cyclobutylcarbonyl, cyclopentylcarbonyl, cyclohexylcarbonyl, cyclopropylsulphonyl, cyclobutylsulphonyl, cyclopentylsulphonyl or cyclohexylsulphonyl, in each case optionally substituted by fluorine, chlorine, bromine, cyano, methyl, ethyl or n- or i-propyl, or represents phenylmethyl, phenylcarbonyl, phenylmethylcarbonyl, phenoxycarbonyl, phenylsulphonyl, phenylmethylsulphonyl, thienylsulphonyl, pyrazolylsulphonyl or pyridinylsulphonyl (which are in each case optionally substituted by fluorine, chlorine, bromine, cyano, methyl, ethyl, n- or i-propyl, n-, i-, s- or t-butyl, trifluoromethyl, methoxy, ethoxy, difluoromethoxy, trifluoromethoxy, methoxycarbonyl or ethoxycarbonyl), $R^3$ represents methyl, ethyl, n- or i-propyl, n-, i-, s- or t-butyl, propenyl, butenyl, propinyl or butinyl, in each case optionally substituted by fluorine, chlorine, cyano, methoxy or ethoxy, or represents cyclopropyl, cyclobutyl, cyclopentyl, cyclohexyl, cyclopropylmethyl, cyclobutylmethyl, cyclopentylmethyl or cyclohexylmethyl, in each case optionally substituted by fluorine, chlorine, bromine, cyano, methyl, ethyl or n- or i-propyl, or represents phenyl or phenylmethyl, in each case optionally substituted by fluorine, chlorine, bromine, cyano, nitro or carboxyl, or by methyl, ethyl, n- or i-propyl, n-, i-, s- or t-butyl, methoxy, ethoxy, methylthio, ethylthio, methylsulphinyl, ethylsulphinyl, methylsulphonyl or ethylsulphonyl (which are in each case optionally substituted by fluorine and/or chlorine), or by dimethylaminosulphonyl or dimethylaminocarbonyl, or by methoxycarbonyl or ethoxycarbonyl (which are in each case optionally substituted by fluorine, chlorine, methoxy or ethoxy), or by phenyl or phenoxy, or represents thienyl, pyrazolyl, pyridinyl or pyridinylmethyl, in each case optionally substituted by fluorine, chlorine, bromine, cyano or nitro, or by methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl, ethylsulphonyl, methoxycarbonyl or ethoxycarbonyl (which are in each case optionally substituted by fluorine and/or chlorine), or by phenyl or phenoxy, and Het represents one of the heterocyclic groupings listed below (bonded via N)

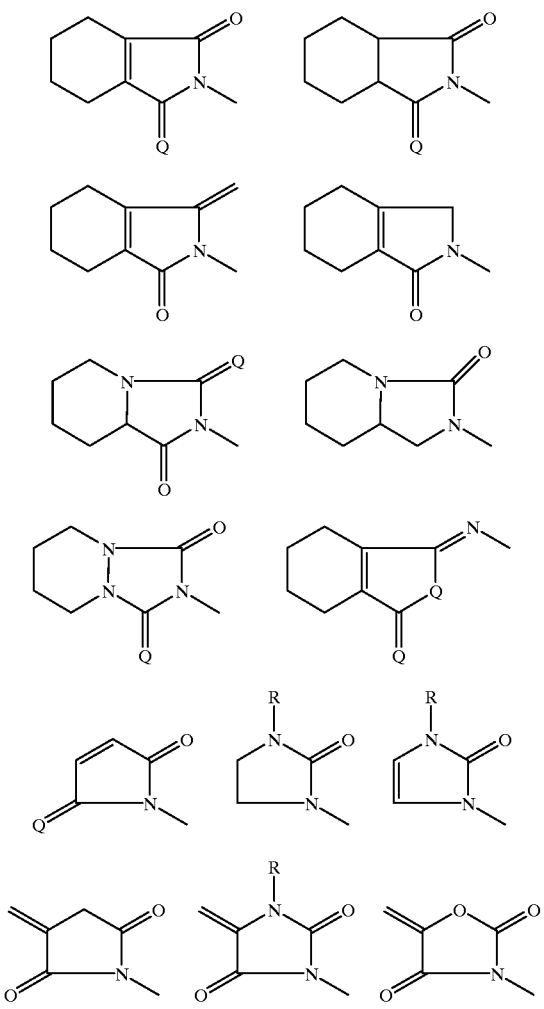

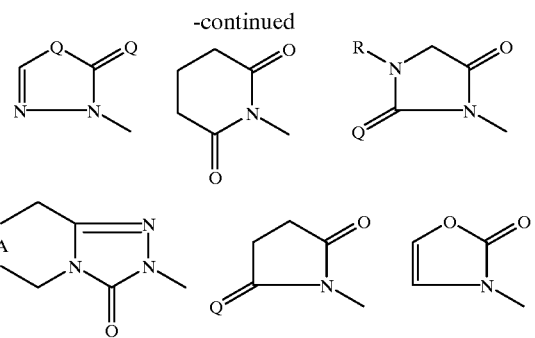

wherein in each case, where appropriate,

A represents methylene, dimethylene or trimethylene and

Q represents oxygen, and wherein the heterocyclic groupings mentioned are in each case optionally substituted once or twice by identical or different radicals from the series consisting of hydroxyl, fluoride, chloride, bromine, cyano, nitro, methyl, ethyl, n- or i-propyl, trifluoromethyl, methoxy, ethoxy, n- or i -propoxy, difluoromethoxy, trifluoromethoxy or phenyl and R represents a radical from the series consisting of hydrogen, hydroxyl, cyano, nitro, $C_1$–$C_4$-alkyl, $C_1$–$C_4$-halogenoalkyl, $C_1$–$C_4$-alkoxy, $C_1$–$C_4$-halogenoalkoxy or phenyl.

The abovementioned definitions of radicals given generally or in preferred ranges apply both to the end products of the formula (I) and also correspondingly to the particular starting substances or intermediate products required for the preparation.

These definitions of radicals can be combined with one another as desired, that is to say also between the stated ranges of preferred compounds.

If, for example, dimethylmaleic anhydride and 4-amino-5-fluoro-2-bis-methylsulphonyl)amino-benzonitrile are used as starting substances, the course of the reaction in process (a) according to the invention can be outlined by the following equation:

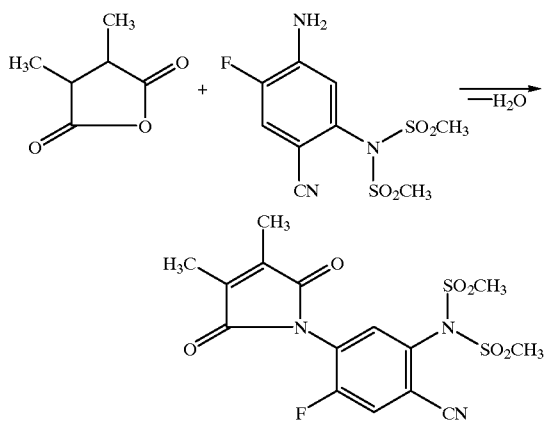

If, for example, N-(4-cyano-2,5-difluoro-phenyl)3,4,5,6-tetydrophthalimide and methanesulphonamide are used as starting substances, the course of the reaction in process (b) according to the invention can be outlined by the following equation:

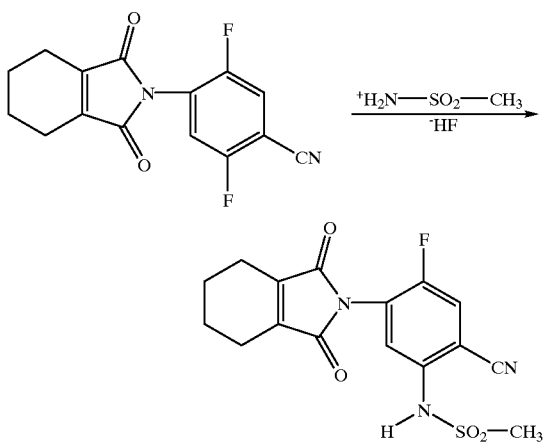

Formulae (IIa) to (IIg) provide general definitions of the anhydrides to be used as starting substances in process (a) according to the invention for the preparation of the compounds of the general formula (I). In the formulae (IIa) to (IIg), Q preferably or in particular has that meaning which has already been mentioned above as preferred or as particularly preferred for Q in connection with the description of the compounds of the formula (I).

The starting substances of the formulae (IIa) to (IIg) are known organic synthesis chemicals.

Formula (III) provides a general definition of the aminobenzonitriles furthermore to be used as starting substances in process (a) according to the invention. In the formula (III), $R^1$, $R^2$ and $R^3$ preferably or in particular have those meanings which have already been mentioned above as preferred or as particularly preferred for $R^1$, $R^2$ and $R^3$ in connection with the description of the compounds of the formula (I).

The starting substances of the formula (III) are not yet known from the literature; however, they are the subject of a prior patent application which has not previously been published (cf DE-P 4335438 of 18.10.1993).

The aminobenzonitriles of the formula (III) are obtained by a procedure in which corresponding halogen compounds of the general formula (VI)

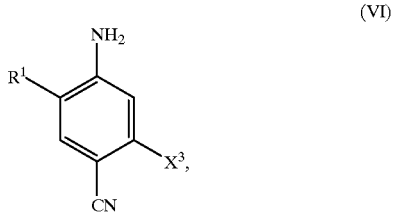

in which
$R^1$ has the abovementioned meaning and
$X^3$ represents halogen (in particular fluorine or chlorine),
are reacted with sulphonamides of the general formula (V)—above—if appropriate in the presence of an acid acceptor, such as, for example, sodium hydride, potassium carbonate or potassium t-butylate, and if appropriate in the presence of a diluent, such as, for example, N-methylpyrrolidone or dimethyl sulphoxide, at temperatures between 100° C. and 200° C.

Possible diluents for carrying out process (a) according to the invention are the customary organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, methylene chloride, chloroform and carbon tetrachloride; ethers, such as diethyl ether, diisopropyl ether, dioxane, tetrahydrofuran or ethylene glycol dimethyl or diethyl ether, ketones, such as acetone, butanone or methyl isobutyl ketone; nitriles, such as acetonitrile, propionitrile or benzonitrile; carboxylic acids, such as acetic acid or propionic acid; carboxylic acid amides, such as N,N-dimethylformamide, N,N-dimethylacetamide, N-methylformanilide, N-methyl-pyrrolidone or hexamethylphosphoric acid triamide; esters, such as methyl acetate or ethyl acetate, sulphoxides, such as dimethyl sulphoxide, or sulphones such as tetramethylene sulphone.

If appropriate, process (a) according to the invention can be carried out in the presence of a reaction auxiliary. Reaction auxiliaries which are preferably used are inorganic or organic acids, such as, for example, acetic acid, methanesulphonic acid, benzenesulphonic acid or p-toluenesulphonic acid, anhydrides, such as, for example, acetic anhydride, or acid chlorides, such as, for example, acetyl chloride. It is also possible to employ other dehydrating agents, such as, for example, dicyclohexylcarbodiimide, or acylation catalysts, such as, for example, 4-dimethylamino-pyridine, as reaction auxiliaries.

The reaction temperatures can be varied within a substantial range in carrying out process (a) according to the invention. The reaction is in general carried out at temperatures between 0° C. and 200° C., preferably at temperatures between 20° C. and 150° C.

Process (a) according to the invention is in general carried out under normal pressure. However, it is also possible to carry out the process under increased or reduced pressure—in general under between 0.1 bar and 10 bar.

For carrying out process (a) according to the invention, the particular starting substances required are in general employed in approximately equimolar amounts. However, it is also possible to use one of the two particular components employed in a larger excess. The reactions are in general carried out in a suitable diluent in the presence of a reaction auxiliary, and the reaction mixture is stirred at the particular required temperature for several hours. Working up in the process according to the invention is in each case carried out by customary methods (cf. the preparation examples).

Formula (IV) provides a general definition of the halogenated heterocyclylbenzonitriles to be used as starting substances in process (b) according to the invention for the preparation of the compounds of the general formula (I). In the formula (IV), Het and $R^1$ and $R^3$ preferably or in particular have those meanings which have already been mentioned above as preferred or as particularly preferred for Het and $R^1$ in connection with the description of the compounds of the formula (I); $X^1$ preferably represents fluorine, chlorine or bromine, in particular fluorine or chlorine.

The starting substances of the formula (IV) are known and/or can be prepared by known processes (cf. EP-A 364797; preparation examples).

Formula (V) provides a general definition of the sulphonamides furthermore to be used as starting substances in process (b) according to the invention. In the formula (V), $R^2$ and $R^3$ preferably or in particular have those meanings which have already been mentioned above as preferred or as particularly preferred for $R^2$ and $R^3$ in connection with the description of the compounds of the formula (I).

The starting substances of the formula (V) are known organic synthesis chemicals.

Possible diluents for carrying out process (b) according to the invention are the customary organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, methylene chloride, chloroform or carbon tetrachloride; ethers, such as diethyl ether, diisopropyl ether, dioxane, tetrahydrofuran or ethylene glycol dimethyl or diethyl ether, ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric acid triamide; esters, such as methyl acetate or ethyl acetate, sulphoxides, such as dimethyl sulphoxide, and alcohols, such as methanol, ethanol, n- or i-propanol, ethylene glycol monomethyl ether, ethylene glycol monoethyl ether, diethylene glycol monomethyl ether or diethylene glycol monoethyl ether.

Process (b) according to the invention is preferably carried out in the presence of a suitable acid acceptor. Possible acid acceptors are all the customary inorganic or organic bases. These include, for example, alkaline earth metal or alkali metal hydrides, hydroxides, amides, alcoholates, acetates, carbonates or bicarbonates, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, as well as basic organic nitrogen compounds, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

The reaction temperatures can be varied within a substantial range in carrying out process (b) according to the invention. The reaction is in general carried out at temperatures between 0° C. and 200° C., preferably at temperatures between 10° C. and 150° C.

Process (b) according to the invention is in general carried out under normal pressure. However, it is also possible to carry out the process under increased or reduced pressure— in general under between 0.1 and 10 bar.

For carrying out process (b) according to the invention, the particular starting substances required are in general employed in approximately equimolar amounts. However it is also possible to use one of the two particular components employed in a larger excess. The reactions are in general carried out in a suitable diluent in the presence of an acid acceptor, and the reaction mixture is stirred at the particular required temperature for several hours. Working up in the process according to the invention is in each case carried out by customary methods (cf. the preparation examples).

The active compounds according to the invention can be used as defoliants, desiccants, agents for destroying broad-leaved plants and, especially, as weed-killers. By weeds, in the broadest sense, there are to be understood all plants which grow in locations where they are not wanted. Whether the substances according to the invention act as total or selective herbicides depends essentially on the amount use&

The active compounds according to the invention can be used, for example, in connection with the following plants:

Dicotyledon weeds of the genera: Sinapis, Lepidium, Galium, Stellaria, Maticaria, Anthemis, Galinsoga, Chenopodium, Urtica, Senecio, Amaranthus, Portulaca, Xanthium, Convolvulus, Ipomoea, Polygonum, Sesbania, Ambrosia, Cirsiurn, Carduus, Sonchus, Solanum, Rorippa, Rotala, Lindemia, Limium, Veronica, Abutilon, Emex, Datura, Viola, Galeopsis, Papaver Centaurea, Trifolium, Ranunculus and Taraxacum.

Dicotyledon crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleccharis, Scirpus, Paspalum, Ischaemum, Sphenoclea, Dactyloctenium, Agrostis, Alopecurus and Apera.

Monocotyledon crops of the genera: Oryza, Zea, Triticum, Hordeu, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without trees planted. Equally, the compounds can be employed for combating weeds in perennial cultures, for example forest, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The compounds of the formula (I) according to the invention are particularly suitable for selectively controlling monocotyledon and dicotyledon weeds in monocotyledon and dicotyledon crops both by the pre-emergence and by the post-emergence method.

The active compounds can be converted into the customary formulations, such as solutions, emulsions, wettable powders, suspensions, powders, dusting agents, pastes, soluble powders, granules, suspensionemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, suitable solid carriers for granules are: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysis products; suitable dispersing agents are: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weed, the active compounds according to the invention, as such or in the form of their formulations, can also be used as mixtures with known herbicides, finished formulations or tank mixes being possible.

Possible components of the mixtures are known herbicides, such as, for example, anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr, aryl-oxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenhthiazuron; hydroxylamines such as, for example, alloxydim, clethodim, cycloxydim, sethoxydim and tralkoxydim; imidazolinones such as, for example, imazethapyr, imazethabenz, imazapyr and imazaquin; nitriles such as, for example, bromoxynil, dichlobenil and ioxynil; oxyacetamides such as, for example, mefenacet; sulphonylureas such as, for example, arnidosulfuron, bensulfuron-methyl, chlorimuron-ethyl, chlorsulfuron, cinosulfuror, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect In general, the amounts used are between 10 g and 10 kg of active compound per hectare of soil surface, preferably between 50 g and 5 kg per ha.

The preparation and use of the active compounds according to the invention can be seen from the following examples.

PREPARATION EXAMPLES

Example 1

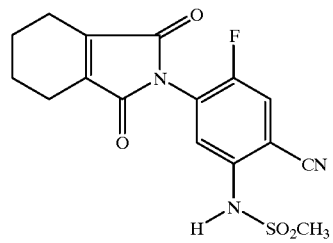

(Process (a))

A mixture of 0.76 g (5 mmol) of 3,4,5,6-tetrahydrophthalic anhydride, 1.15 g (5 mmol) of 4-amino-5-fluoro-2-methylsulphonylamino-benzonitrile and 10 ml of acetic acid is heated under reflux (about 120° C.) with a spatula-tip of 4-dimethylamino-pyridine for 30 hours and is then concentrated The residue is digested with a mixture of water, diethyl ether and ethyl acetate and the product obtained as crystals is isolated by filtration with suction.

0.60 g (33% of theory) of N-4-cyano-2-fluoro-5-methylsulphonylaminophenyl)-3,4,5,6-tetrahydrophthalimide of melting point 113° C. is obtained.

Example 2

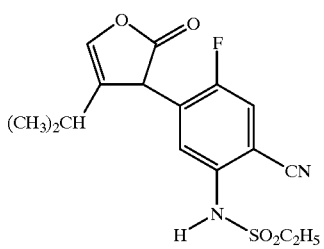

(Process (b))

A mixture of 0.80 g (3.0 mmol) of 3-(4-cyano-2,5-difluoro-phenyl)-4-isopropyl-oxazolin-2-one, 0.36 g (3.3 mmol) of ethanesulphonamide, 0.46 g (3.3 mmol) of potassium carbonate and 50 ml of dimethylsulphoxide is stirred at 120° C. for 3 hours and then poured onto ice-water, acidified with concentrated hydrochloric acid and shaken with methylene chloride. The organic phase is separated off, dried with sodium sulphate and filtered. The solvent is carefully distilled off from the filtrate under a waterpump vacuum.

0.60 g (57% of theory) of 3-4-cyano-2-fluoro-5-ethylsulphonylamino-phenyl)-4-isopropyl-oxazolin-2-one is obtained as an oily residue.

The compounds of the formula (I) listed in the following Table 1, for example, can also be prepared analogously to Examples 1 and 2 and in accordance with the general description of the preparation processes according to the invention.

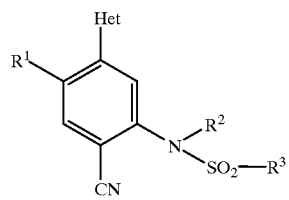

(I)

TABLE 1

Examples of compounds of the formula (I)

| Example No. | Het | $R^1$ | $R^2$ | $R^3$ | Melting point (° C.) |
|---|---|---|---|---|---|
| 3 | ![tetrahydrophthalimide-N-methyl] | F | H | $C_2H_5$ | 90 |
| 4 | ![tetrahydrophthalimide-N-methyl] | F | $CH_3$ | $C_2H_5$ | 126 |
| 5 | ![4-trifluoromethyl-glutarimide-N-methyl, F3C substituent] | F | H | $C_2H_5$ | 160 |
| 6 | ![3,4-dimethylmaleimide-N-methyl, H3C, H3C] | F | H | $C_2H_5$ | 132 |
| 7 | ![3-methylmaleimide-N-methyl, H3C] | F | H | $C_2H_5$ | 139 |

TABLE 1-continued

Examples of compounds of the formula (I)

| Example No. | Het | R$^1$ | R$^2$ | R$^3$ | Melting point (° C.) |
|---|---|---|---|---|---|
| 8 | (tetrahydroisoindolinone with OH) | F | H | C$_2$H$_5$ | (amorphous) |
| 9 | (3,4-dimethyl-maleimide, N-methyl) | F | CH$_3$ | C$_2$H$_5$ | 154 |
| 10 | (3-isopropylidene-succinimide, N-methyl) | F | H | C$_2$H$_5$ | 75 |
| 11 | (4-trifluoromethyl-glutarimide, N-methyl) | F | H | CH$_3$ | 233 |
| 12 | (4-methyl-glutarimide, N-methyl) | F | H | CH$_3$ | 188 |
| 13 | (3-methyl-maleimide, N-methyl) | F | H | CH$_3$ | 146 |
| 14 | (3-isopropylidene-succinimide, N-methyl) | F | H | CH$_3$ | 139 |
| 15 | (triazolo-azepinone) | F | H | C$_2$H$_5$ | 208 |

TABLE 1-continued

Examples of compounds of the formula (I)

| Example No. | Het | R¹ | R² | R³ | Melting point (° C.) |
|---|---|---|---|---|---|
| 16 | (6,6-dimethyl-5,6,7,8-tetrahydro-[1,2,4]triazolo[4,3-a]pyridin-3(2H)-one, 2-methyl) | F | H | $C_2H_5$ | 125 |
| 17 | (6,6-dimethyl-5,6,7,8-tetrahydro-[1,2,4]triazolo[4,3-a]pyridin-3(2H)-one, 2-methyl) | F | H | $CH_3$ | 185 |
| 18 | (2-methyl-6,7,8,9-tetrahydro-5H-[1,2,4]triazolo[4,3-a]azepin-3(2H)-one) | F | H | $CH_3$ | 194 |
| 19 | (2-methyl-5,6,7,8-tetrahydro-[1,2,4]triazolo[4,3-a]pyridin-3(2H)-one) | F | H | $CH_3$ | 205 |
| 20 | (2-methyl-5,6,7,8-tetrahydro-[1,2,4]triazolo[4,3-a]pyridin-3(2H)-one) | F | H | $C_2H_5$ | 197 |
| 21 | (2-methyl-6,7-dihydro-5H-pyrrolo[2,1-c][1,2,4]triazol-3(2H)-one) | F | H | $CH_3$ | 228 |
| 22 | (2-methyl-6,7-dihydro-5H-pyrrolo[2,1-c][1,2,4]triazol-3(2H)-one) | F | H | $C_2H_5$ | 176 |
| 23 | (2-methyl-5,6,7,8-tetrahydro-[1,2,4]triazolo[4,3-a]pyridin-3(2H)-one) | F | H | $CH(CH_3)_2$ | 205 |
| 24 | (2-methyl-5,6,7,8-tetrahydro-[1,2,4]triazolo[4,3-a]pyridin-3(2H)-one) | F | H | cyclopropyl | 201 |

TABLE 1-continued

Examples of compounds of the formula (I)

| Example No. | Het | R¹ | R² | R³ | Melting point (° C.) |
|---|---|---|---|---|---|
| 25 | hexahydroimidazo[1,5-a]pyridine-1,3-dione, N-methyl | F | H | $CH_3$ | 110 |
| 26 | 4,5,6,7-tetrahydroisoindole-1,3-dione, N-methyl | F | H | $C_3H_7$-n | |
| 27 | 4,5,6,7-tetrahydroisoindole-1,3-dione, N-methyl | F | —$COCH_3$ | $C_2H_5$ | |
| 28 | 4-trifluoromethyl-N-methylglutarimide | F | $CH_3$ | $CH_3$ | |
| 29 | 4-trifluoromethyl-N-methylglutarimide | F | —$SO_2CH_3$ | $CH_3$ | |
| 30 | 4-trifluoromethyl-N-methylglutarimide | Cl | H | $C_2H_5$ | |
| 31 | 4-trifluoromethyl-N-methylglutarimide | F | $CH_2COOCH_3$ | $CH_3$ | |
| 32 | 4-trifluoromethyl-N-methylglutarimide | F | H | $CF_3$ | |

TABLE 1-continued

Examples of compounds of the formula (I)

| Example No. | Het | R¹ | R² | R³ | Melting point (° C.) |
|---|---|---|---|---|---|
| 33 | 4,5,6,7-tetrahydroisoindole-1,3-dione (N-linked) | F | H | $CF_3$ | |
| 34 | 4,5,6,7-tetrahydroisoindole-1,3-dione (N-linked) | F | $-SO_2CH_3$ | $CH_3$ | |
| 35 | 3,4-dimethyl-pyrrole-2,5-dione (N-linked) | F | H | $CF_3$ | |
| 36 | 3,4-dimethyl-pyrrole-2,5-dione (N-linked) | F | $-SO_2CH_3$ | $CH_3$ | |
| 37 | 4,5,6,7-tetrahydroisoindole-1,3-dione (N-linked) | H | $-SO_2Et$ | $CH_3$ | |
| 38 | 4,5,6,7-tetrahydroisoindole-1,3-dione (N-linked) | H | H | Et | |
| 39 | 4-(trifluoromethyl)piperidine-2,6-dione (N-linked) | H | $-SO_2CH_3$ | $CH_3$ | |
| 40 | 4-(trifluoromethyl)piperidine-2,6-dione (N-linked) | H | H | $CH_3$ | |

TABLE 1-continued

Examples of compounds of the formula (I)

| Example No. | Het | R¹ | R² | R³ | Melting point (° C.) |
|---|---|---|---|---|---|
| 41 | 3,4-dimethyl-maleimide (H₃C, H₃C substituents) | F | H | $CH_3$ | 135 |
| 42 | 3-hydroxy-3-methyl-tetrahydroisoindolin-1-one | F | H | $CH_3$ | 135 |
| 43 | 3-trifluoromethyl-maleimide | F | H | $CH_3$ | 93 |
| 44 | 3-methylene-tetrahydroisoindolin-1-one | F | H | $CH_3$ | 150 |
| 45 | tetrahydroisoindoline-1,3-dione | F | $-SO_2C_2H_5$ | $C_2H_5$ | 210 |
| 46 | 5,6,7,8-tetrahydro-[1,2,4]triazolo[4,3-a]pyridin-3(2H)-one | F | $CH_3$ | $C_2H_5$ | 142 |
| 47 | 5,6,7,8-tetrahydro-[1,2,4]triazolo[4,3-a]pyridin-3(2H)-one | F | $-SO_2CH_3$ | $C_2H_5$ | 196 |
| 48 | 5,6,7,8-tetrahydro-[1,2,4]triazolo[4,3-a]pyridin-3(2H)-one | F | $-SO_2C_2H_5$ | $C_2H_5$ | 196 |

TABLE 1-continued

Examples of compounds of the formula (I)

| Example No. | Het | R¹ | R² | R³ | Melting point (° C.) |
|---|---|---|---|---|---|
| 49 | ![structure] | F | —CH$_2$COOC$_2$H$_5$ | C$_2$H$_5$ | 193 |
| 50 | ![structure] | F | —SO$_2$C$_2$H$_5$ | C$_2$H$_5$ | 164 |
| 51 | ![structure] | F | H | CH$_3$ | |
| 52 | ![structure] | F | H | C$_2$H$_5$ | |

Starting substances of the formula (III):

Example (III-1)

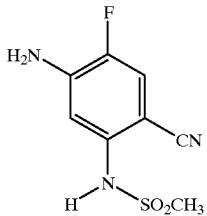

A mixture of 92.4 g (0.6 mol) of 4-cyano-2,5-difluoro-aniline, 60 g (0.60 mol) of methanesulphonamide, 166 g of potassium carbonate and 80 ml of N-methyl-pyrrolidone is heated at 180° C. for 10 hours. After cooling the mixture is stirred into 5 liters of water and the resulting solution is washed twice with 400 ml of ethyl acetate each time. The aqueous phase is then covered with a layer of 300 ml of ethyl acetate and acidified with 10% strength hydrochloric acid The product obtained as crystals is then isolated by filtration with suction.

70 g (51% of theory) of N-(5-amino-2-cyano4-fluoro-phenyl)-methanesulphonamide of melting point 238° C. are obtained.

Starting substances of the formula (IV):

Example (IV-1)

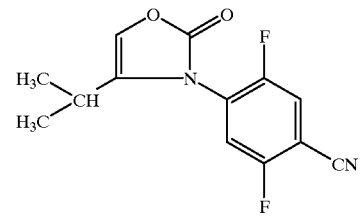

A mixture of 2.0 g (16 mmol) of 4-isopropyl-oxazolin-2-one, 2.5 g (16 mmol) of 2,4,5-trifluoro-benzonitrile, 2.8 g (20 mmol) of potassium carbonate and 50 ml of dimethyl sulphoxide is stirred at 60° C. for 15 hours, subsequently diluted to about three times the volume with water and acidified with concentrated hydrochloric acid. The organic phase is separated off, diluted with methylene chloride, dried with sodium sulphate and filtered. The filtrate is concentrated and the residue is recrystallized from isopropanol.

0.80 g (19% of theory) of 3-(4-cyano-2,5-fluoro-phenyl)-4-isopropyl-oxazolin-2-one of melting point 83° C. is obtained.

The compounds of the formula (IV) listed in the following Table 2, for example, can also be prepared analogously to Example (IV-1).

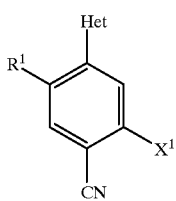

(IV)

TABLE 2

Examples of the compounds of the formula (IV)

| Example No. | Het | R¹ | X¹ | Melting point (° C.) |
|---|---|---|---|---|
| (IV-2) | 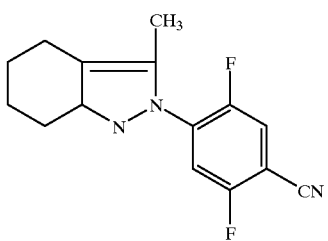 | F | F | 103 |
| (IV-3) | 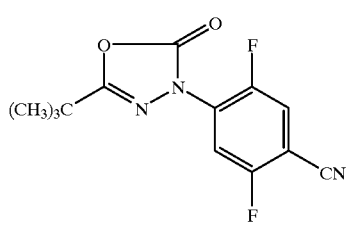 | F | F | 168 |

Use Examples

The following compounds are used as comparison material in the use examples below:

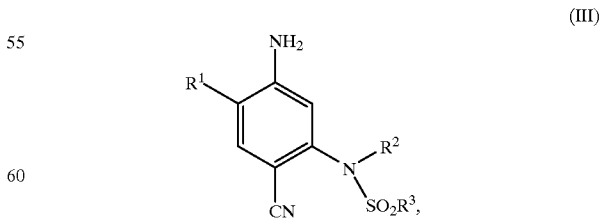

(A)

2,5-Difluoro-4-(4,5,6,7-tetrahydro-3-methyl-2H-indazol-2-yl)-benzonitrile (known from EP-A 370332, Example 2).

(B)

4-[5-(t-Butyl)-2-oxo-1,3,4-oxadiazol-3(2H)-yl]-2,5-difluoro-benzonitrile (known from EP-A 370332, Example 7).

Example A
Pre-emergence test
Solvent: 5 parts by weight of acetone
Emulsifier: 1 part by weight of allaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, for example, the compounds according to Preparation Examples 3 and 5 show, with a good tolerance and and amounts applied of 125 g/ha with respect to crop plants, such as, for example, barley (0%), a potent action against weeds, such as Abutilon (100%), Amaranthus (100%), Chenopodium (90–100%), Datura (80–100%), Galinsoga (95–100%), Portulaca (100%) and Solanurn (80–100%).

Example B
Post-emergence test
Solvent: 5 parts by weight of acetone
Emulsifier: 1 part by weight of alklylaryl polyglycol ether To produce a suitable preparation of active compound, 1 part by weight of active compound is mixed with the stated amount of solvent, the stated amount of emulsifier is added and the concentrate is diluted with water to the desired concentration Test plants which have a height of 5–15 cm are sprayed with the preparation of the active compound in such a way as to apply the particular amounts of active compound desired per unit area. After three weeks, the degree of damage to the plants is rated in % damage in comparison to the development of the untreated control. The figures denote:

0%=no action (like untreated control)
100%=total destruction

In this test, for example, the compounds according to Preparation Examples 1, 3 and 5 show, when applied in amounts of 30 g/ha and with a very good tolerance with respect to crop plants, such as, for example, barley, a very potent action against weeds, such as Abutilon (100%), Amaranthus (100%), Chenopodium (95%), Galium (90–95%) and Veronica (100%).

We claim:
1. An aminobenzonitrile of formula (III)

(III)

in which
R¹ represents hydrogen or halogen,
R² represents formyl, or represents alkenyl, alkinyl, alkoxy, alkylcarbonyl, alkoxycarbonyl or alkylsulphonyl having in each case 1 to 6 carbon atoms and which may be substituted in each case by halogen, cyano, $C_1$–$C_4$-alkoxy or $C_1$–$C_4$-alkoxy-carbonyl, or represents cycloalkyl, cycloalkylalkyl, cycloalkylcarbonyl or cycloalkylsulphonyl having 3 to 6 carbon atoms in the individual cycloalkyl moieties and, which may have 1 to 4 carbon atoms in the alkyl moiety and which may be substituted in each case by halogen, cyano or $C_1$–$C_4$-alkyl, or represents phenylmethyl, phenylcarbonyl, naphthylcarbonyl, phenylmethylcarbonyl, phenoxycarbonyl, phenylsulphonyl, naphthylsulfonyl or phenylmethylsulphonyl, which may be substituted in each case by halogen, cyano, $C_1$–$C_1$-alkyl, $C_1$–$C_1$-halogenoalkyl, $C_1$–$C_4$-alkoxy, $C_1$–$C_4$-halogenoalkoxy or $C_1$–$C_4$-alkoxycarbonyl, $R^3$ represents alkyl having in each case 1 to 10 carbon atoms and which may be substituted in each case by halogen, cyano or $C_1$–$C_4$-alkoxy, or represents cycloalkyl having 3 to 8 carbon atoms and which may be substituted in each case by halogen, cyano or $C_1$–$C_4$-alkyl, or represents carbocyclic aryl or carbocyclic arylalkyl having 6 or 10 carbon atoms in the aryl moiety and 1 to 4 carbon atoms in the alkyl moiety and which may be substituted in each case by halogen, cyano, nitro, carboxyl or carbamoyl, by $C_1$-$C_4$-alkyl, $C_1$–$C_4$-alkoxy, $C_1$–$C_4$-alkylthio, $C_1$–$C_4$-alkylsulphinyl or $C_1$–$C_4$-alkylsulphonyl which may be substituted in each case by fluorine or chlorine, or by dimethylaminosulphonyl, diethylaminosulphonyl, dimethylaminocarbonyl or diethylaminocarbonyl, or by $C_1$–$C_4$-alkoxy-carbonyl which may be substituted in each case by halogen, methoxy or ethoxy, or by phenyl, phenyloxy or phenylthio which may be substituted in each case by halogen, cyano, methyl, methoxy, trifluoromethyl or trifluoromethoxy.

\* \* \* \* \*